United States Patent
Fang

(10) Patent No.: US 9,999,760 B2
(45) Date of Patent: Jun. 19, 2018

(54) DVDMS SENSITIZER FOR CANCER SONODYNAMIC THERAPY

(71) Applicant: Wei Fang, Cape Coral, FL (US)

(72) Inventor: Qicheng Fang, Beijing (CN)

( * ) Notice: Subject to any disclaimer, the term of this patent is extended or adjusted under 35 U.S.C. 154(b) by 0 days. days.

(21) Appl. No.: 14/872,470

(22) Filed: Oct. 1, 2015

(65) Prior Publication Data

US 2017/0095557 A1   Apr. 6, 2017

(51) Int. Cl.
*A61K 31/409* (2006.01)
*A61M 37/00* (2006.01)
*A61K 41/00* (2006.01)

(52) U.S. Cl.
CPC ....... *A61M 37/0092* (2013.01); *A61K 31/409* (2013.01); *A61K 41/0033* (2013.01)

(58) Field of Classification Search
CPC ............ A61K 41/0047; A61K 41/0057; A61K 31/409; A61M 37/0092
See application file for complete search history.

(56) References Cited

PUBLICATIONS

Li et al, Biopharmaceutics & Drug Disposition, 2014, vol. 35, issue 1.*
Wang et al, International Journal of Nanomedicine, 2014, 9, 3077-3090.*
Wang et al, Ultrasonic, 2011, 51, 539-546.*
Song et al, Onco Targets and Therapy, 2014, 7, 1801-1810.*

* cited by examiner

*Primary Examiner* — Sudhakar Katakam

(57) ABSTRACT

A method for treatment of hyperproliferative tissue by injection of and subsequently exposing the hyperproliferative tissue to a frequency of ultrasound. The invention further includes purified bis [1-[6,7-bis [2-(sodium carbonate ethyl]-1,3,5,8,-tetramethyl-2-vinyl-porphin-4-yl]ethyl] ether (DVDMS) for use in sonodynamic treatment of hyperproliferative tissue including cancer and further includes a kit including a dosage controllable injection device charged with a biologically compatible fluid containing DVDMS.

9 Claims, 9 Drawing Sheets

Bis[1-[6,7-bis[2-(sodium carbonate) ethyl]1,3,5,8,-tetra- methyl-2-vinyl- porphin-4-yl]-ethyl]ether (DVDMS)

A cold spray mass spectrum of the compound of Figure 1.

HPLC of protoporphyrin dimethyl ester (DVDMS)

Reaction Scheme

Protoporphyrin dimethyl ester

↓ HBr/CH$_2$Cl$_2$

DVDME-2

$C_{72}H_{78}N_8O_9$

MW: 1198

Bis[1-[6,7-bis[2-(methoxycarbonyl)ethyl]-1,3,5,8-tetramethyl-2-vinylporphin-4-yl]ethyl] Ether ↓ NaOH

DVDMS-2

$C_{68}H_{66}N_8O_9Na_4$

MW: 1230

Bis[1-[6,7-bis-sodium propionate-1,3,5,8-tetramethyl]
2-vinylporphin-4-yl]ethyl] ether (DVDMS)

HPLC of bis [1- [6,7-bis[2-(methoxycarbonyl)ethyl] -1,3,5,8-tetramethyl- 2-vinyl porphin-4-yl]-ethyl]ether (DVDME-2)

DVDMS SENSITIZER FOR CANCER SONODYNAMIC THERAPY

BACKGROUND OF THE INVENTION

In recent years, cancer has become, of the major diseases, a most serious threat to human health. The World Health Organization (WHO) 2008 statistics show that the global number of cancer deaths worldwide is about 11 million new cases of cancer each year, with the Asia-Pacific region accounting for 45 percent of new cases of cancer worldwide, and through new cases of cancer each year, up to 7 million patients die. In the past 30 years, the rate of cancer incidence has grown by 3%-5% annually, with three out of four new cases occurring in the newly industrialized and developing countries, with the number of cancer deaths in the Asia-Pacific region accounting for about half of cancer deaths worldwide.

The growth in incidence of cancer has occurred despite some advances in treatment beyond the use of harsh chemicals, surgery and ionizing radiation.

One of these advances, toward the end of the twentieth century, is photodynamic therapy, especially with the introduction of the hematoporphyrin Photofrin™. See Pandey R. K; Smith K. M; Dougherty T. J: Porphyrin Dimers as Photosensitizers in Photodynamic Therapy. *J. Med. Chem.*, 1990, 33, 2032-2038 and Byrne C. J; Morris I. K. Ward A. D: The Synthesis of the Dimer and Trimer Ether-Linked Components of Hematoporphyrin Derivative. *Aust. J. Chem.*, 1990, 43, 1889-1907.

Photodynamic therapy is accomplished by systemic introduction of a photosensitizer, e.g. Photofrin™ that selectively accumulates into hyperproliferative tissues, such as cancer, followed by treatment with an activating wavelength of light that causes development of singlet oxygen that kills the cancer cells. Photodynamic therapy is thus much less invasive than traditional treatments and is highly selective for cancer cells thus greatly reducing side effects such as death or injury to normal cells or interference with normal physiological activities.

Photodynamic therapy, nevertheless has limitations of its own. Among such limitations are the possibility of serious subsequent light sensitivity, at least until the photosensitizer clears the system or is metabolized. An even more significant problem is the fact that photodynamic therapy only works in areas close to a surface, e.g. the skin, from which light can penetrate and penetration depth is extremely limited.

Porfimer sodium (Photofrin™), previously discussed, is in fact a mixture of a large number related compounds. The compound Bis[1-[6,7-bis[2-(sodium carbonate)ethyl]1,3,5,8,-tetra-ethyl-2-vinyl-porphin-4-yl]-ethyl]ether (DVDMS) has recently been purified from that mixture and has been found to be superior to porfimer sodium both in efficacy and with respect to reduction of the side effect of subsequent light sensitivity. The structural formula of DVDMS is believed to be represented in FIG. 1 and a cold spray spectrum of DVDMS is shown in FIG. 2.

It has recently been discovered that some compounds might be used as treatment aids that are activated by ultrasound rather than or in addition to light. This has become known as sonodynamic therapy. Unfortunately, up to now, compounds tested have not been as effective as desired and in any case have often required high dosages to have effect.

The concept is similar to the more established photodynamic therapy (PDT) except light, instead of ultrasound, is used to activate the sensitizer. Sonodynamic therapy (SDT) offers significant advantages over PDT because ultrasound is widely accepted as a cost-effective and safe clinical imaging modality and, unlike light, can be tightly focused with penetration in soft tissue up to several tens of centimeters depending on the frequency used. This therefore enables the potential of treating deeper-rooted tumors than is currently possible with PDT.

BRIEF SUMMARY OF THE INVENTION

Figure 1:
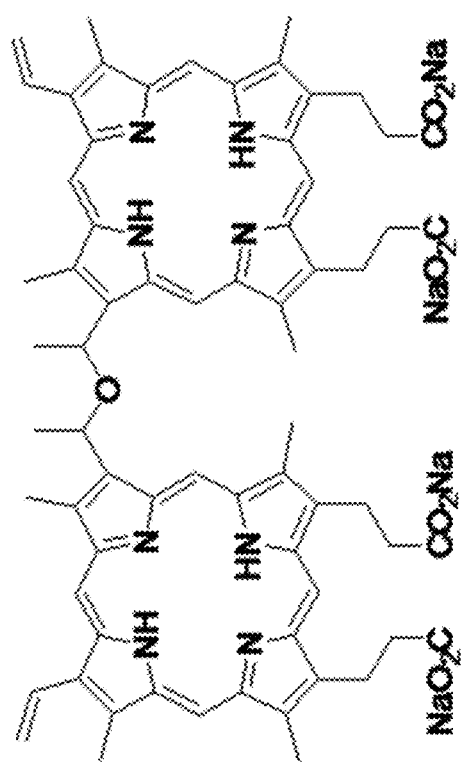
FIG. 1 shows a schematic formula for bis [1-[6,7-bis [2-(sodium carbonate ethyl]-1,3,5,8,-tetramethyl-2-vinyl-porphin-4-yl]ethyl]ether, also referred to herein as DVDMS and Sinoporphyrin Sodium-SDT.

The invention includes the compound purified bis [1-[6, 7-bis [2-(sodium carbonate ethyl]-1,3,5,8,-tetramethyl-2-vinyl-porphin-4-yl]ethyl]ether (DVDMS) for use in sonodynamic therapy, a method for treatment of hyperproliferative tissue by injection of (DVDMS) and subsequently exposing the hyperproliferative tissue to a frequency of ultrasound and further includes a kit including a sonodynamic dosage controllable injection device charged with a biologically compatible fluid containing DVDMS.

DVDMS is an active component isolated from Photofrin™ II. The efficacy of DVDMS in sonic treatment is about ten times higher than Photofrin™ II when injected into a host where it accumulates in hyperproliferative tissue, e.g. tumor tissue, to a much higher degree than surrounding normal tissues. Subsequent to injection, the tumor tissue is exposed to a particular low intensity ultrasound and in the presence of molecular oxygen, DVDMS become cytotoxic and destroys the hyperproliferative tissue without causing irreversible normal tissue damage. DVDMS shows significantly higher autofluorescence intensity and singlet oxygen production efficiency than Photofrin™. In addition, DVDMS has good activity at an appropriate ultrasound intensity and as such is a superior sonosensitizer. The DVDMS mediates sonodynamic therapy (SDT) induced mitochondrial-dependent apoptosis in tumor cells. While not wishing to be bound by any particular theory, it is believed that the apoptosis is due to production of reactive oxygen species (ROS).

DETAILED DESCRIPTION OF THE INVENTION

In accordance with the present invention it has been surprisingly discovered that DVDMS, in addition to being an excellent photosensitizer, is a superior sonodynamic sensitizer. The basic principles of sonodynamic therapy in cancer patients using DVDMS is by injecting DVDMS, using selective tumor cell uptake and retention of the sensitizer to calculate residence time, after which residence time the tumor is irradiated with a specific frequency of ultrasound excitation so that deep tumors in the biological tissue are debilitated or destroyed.

This is believed to occur by inducing a sonically-enabled chemical reaction to produce highly-reactive singlet oxygen, free radicals, and other reactive oxygen species (ROS) components, prompting many kinds of biological molecules, such as amino acids, fatty acids, and adenosine to oxidize, producing a large number of chemical intermediates with oxidative secondary activity, thereby undermining protein, fat, nucleic acids, and other critical cellular components, causing severe damage and obstruction to cellular functions, ultimately leading to irreversible damage and death in tumor cells and other hyperproliferative cells. Moreover, the sensitizer also induces vascular endothelial damage and blood stagnation in microvascular tumor tissue, leading to tissue necrosis in the tumor. The DVDMS sensitizer thus, with two effects, combines both effects to not only kill tumor and other hyperproliferative cells directly, but also block blood vessels in the tumor, inducing tumor tissue hypoxia, nutrition depletion, and also preventing tumor cell proliferation and metastasis.

Sonodynamic therapy with DVDMS therefore has specific target tissue selectivity, has good controllability, low-toxicity, and short treatment time. Sonodynamic therapy with DVDMS can also cause the apoptosis of tumors and other hyperproliferative tissue while minimizing damage to normal tissue, protecting the appearance and function of vital organs and so on.

Sonodynamic therapy with DVDMS is an approach that is an alternative treatment therapy to surgery, radiotherapy, chemotherapy and other known treatments. Sonodynamic, in conjunction with or without photodynamic therapy, can be used for the treatment of various malignant tumors, including esophageal cancer, lung cancer, brain tumors, head and neck cancer, eye cancer, throat cancer, breast tumors, breast cancer, mesothelioma, liver cancer, stomach cancer, abdominal sarcoma, bladder cancer, gynecological cancer, colorectal cancer, and skin cancer. Repeated treatment does not produce drug resistance. Early primary tumors can be successfully cured by sonodynamic therapy, and for more advanced cases of cancer, especially in the old and infirm, or those with heart, lung and kidney dysfunction or patients with hemophilia who can not otherwise undergo surgery or treatment, sonodynamic therapy can, as a palliative treatment, relieve symptoms, reduce pain, improve quality of life and prolong survival time.

It is further believed that sonodynamic therapy with DVDMS is effective against other hyperproliferative tissue such as that found in epidermal hyperplasia, hyperproliferative breast disorder, abnormal esophageal tissue such as found in Barretts Esophagus, coronary hyperproliferation due to stent placement, endometriosis, bone marrow stomal cells and macular degeneration.

The scientific basis of sonodynamic therapy (SDT) using DVDMS relies on the generation of ROS through the simultaneous combination of a sensitizing agent, molecular oxygen and low intensity ultrasound. In the absence of ultrasound, the sensitizing agent is non-toxic and only exerts toxic effects (via. ROS) upon interaction with ultrasound in the presence of molecular oxygen.

The new sonosensitizer bis[1-[6,7-bis[2-(sodium carbonate)ethyl]1,3,5,8-tetra-methyl-2-vinyl-porphin-4-yl]-ethyl] ether (DVDMS) can be synthesized by using the protoporphyrin dimethyl ester as a raw material. The reaction product is separated and purified by silica gel column. The new sonosensitizer is of high purity relative to Phofrin™ Purity for use as a sonosensitizer is at least 90%, preferably at least 95% and most preferably at least 98 percent.

Specific preparation methods and test results are as follows:

Determined by HPLC analysis Agilent 1200 Series HPLC Analyzer:
Analytical conditions:
Analytical column: Shiseido SHISEIDO Capcell C 18 MG 4 6 mm×150 mm×5 m;
Detection wavelength: 380 nm;
Column temperature: 30° C.;
Sample: sample is dissolved in methanol, prior to injection first with 0.45 m nylon microporous filter, membrane filtration;
Mobile phase: methanol and 1% aqueous solution of acetic acid; flow rate: 1.0 mL/min.

TABLE 1

| Time (min) | A: 1% aqueous solution of acetic acid (%) | B: methanol (%) |
| --- | --- | --- |
| 0.0 | 30.0 | 70.0 |
| 30.0 | 10.0 | 90.0 |
| 45.0 | 10.0 | 90.0 |
| 60.0 | 0.0 | 100.0 |
| 70.0 | 0.0 | 100.0 |
| 70.5 | 30.0 | 70.0 |
| 100.5 | 30.0 | 70.0 |

(The last 30 minutes are balanced column, in preparation for the next sample inlet)

Examples: Preparation

Example 1

To a solution of protoporphyrin dimethyl ester (50 g) in anhydrous dichloromethane (100 ml) was added a solution of anhydrous dichloromethane saturated with gaseous hydrogen bromide and the mixture was tightly stoppered in the dark for 24 h. Aqueous dichloromethane (50 ml, 1:1) was added, the organic layer was separated, washed with water and the solvent was removed under reduced pressure. The crude product was separated on silica column chromatography (fineness of silica gel H:200-300 mesh, Qingdao Marine Chemical Factory). Elution with acetone in dichloromethane and collected the eluent, contained the DVDME-2 no less than 20%. The 20% DVDME-2 was rechromatographed on silica in order to get in purity up to 90% of DVDME-2. HPLC retention time: 64 minutes.

Figure 6:
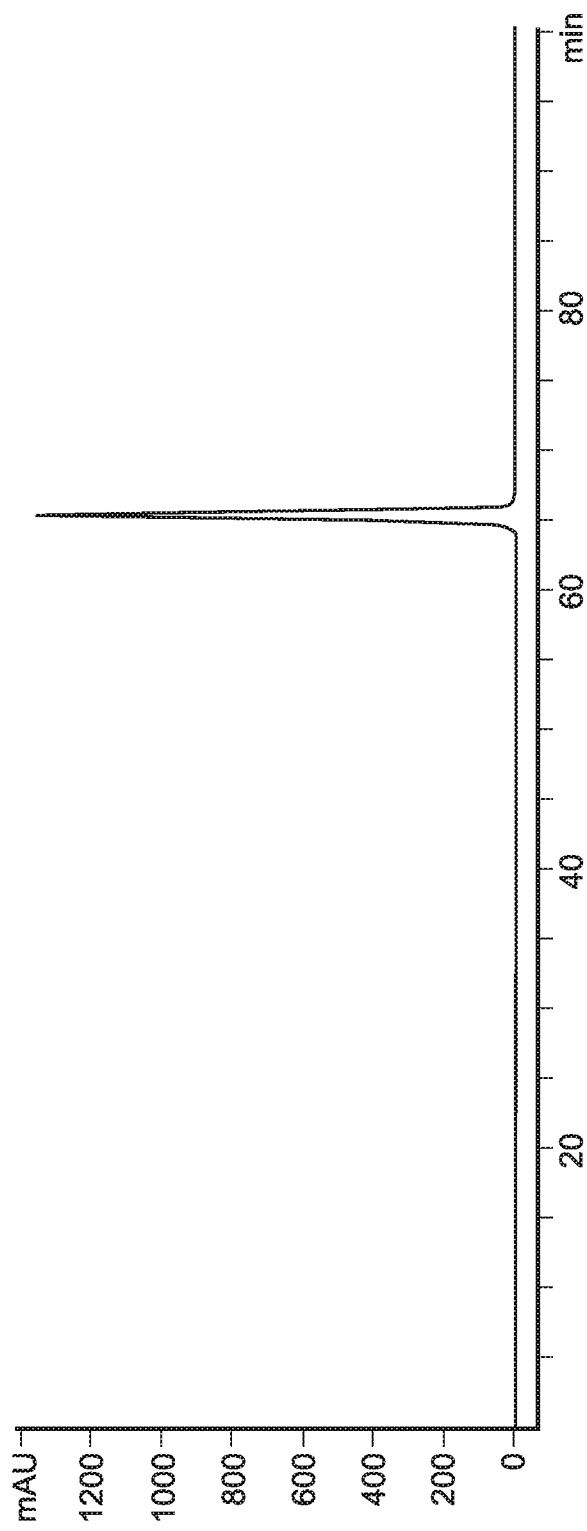
FIG. 6 shows an HPLC elution for bis[1-[6,7-bis[2-(methoxycarbonyl)ethyl]-1,3,5,8-tetramethyl-2-vinylporphin-4-yl]ethyl]ether (DVDME-2) prepared from protoporphyrin dimethyl ester showing purity up to 90 percent.

An HPLC elution for DVDME-2 is shown in FIG. 6.

Figure 7:
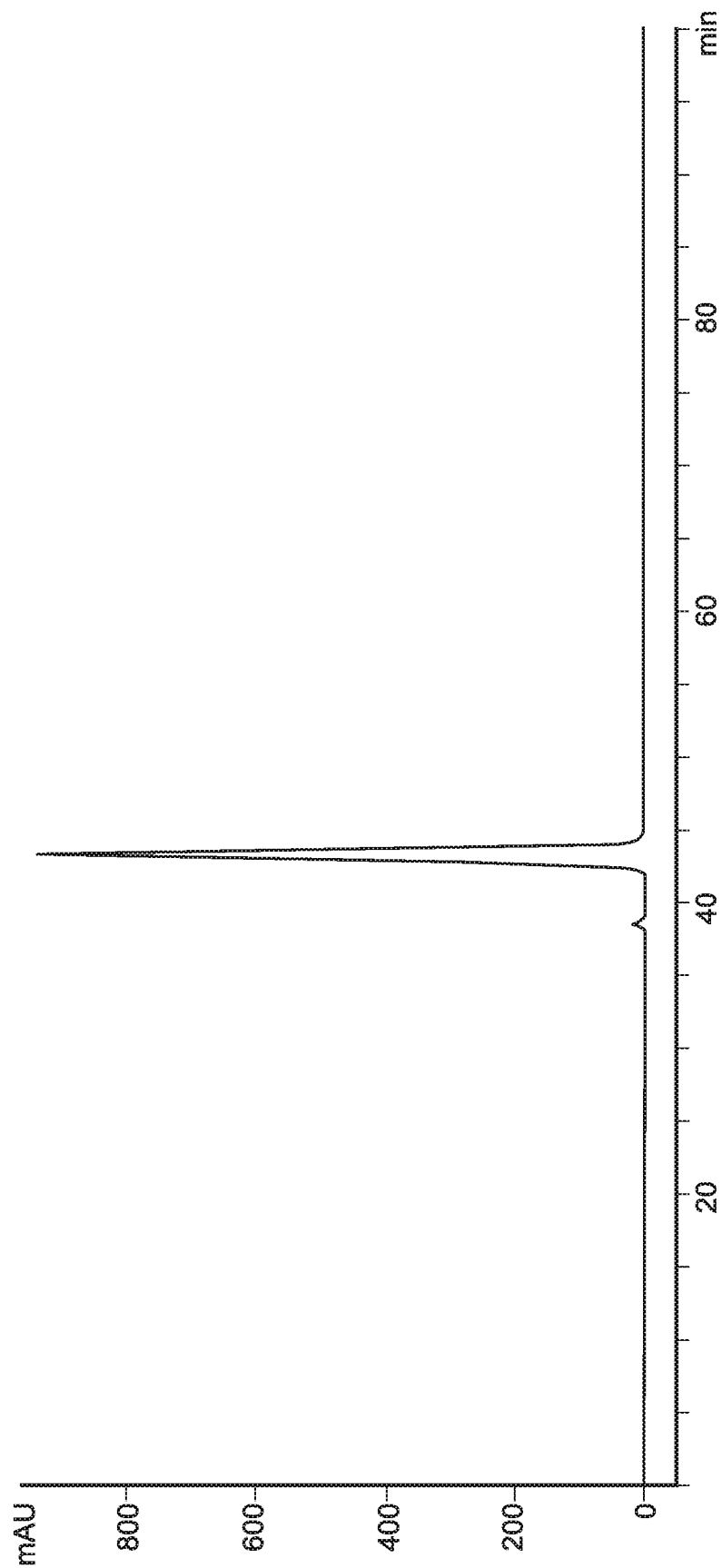
FIG. 7 shows an HPLC elution for DVDMS showing purity higher than 98 percent. The purity of DVDMS relative to Photfrin™ is unmistakable.

5 g of DVDME-2 was dissolved in 400 ml of tetrahydrofuran, add 100 ml 0.1 mol sodium hydroxide solution, shaken well, kept in dark place overnight and then evaporating the tetrahydrofuran solution under reduced pressure. The dried reaction product was eluted into the reflux device, an amount of anhydrous ethanol was added and eluted to remove residual sodium hydroxide and other impurities. The object compound was purified DVDMS-2 (DVDMS). HPLC retention time: 43 minutes, the purity is higher than 98%. An HPLC elution for DVDME-2 is shown in FIG. 7

Figure 2:
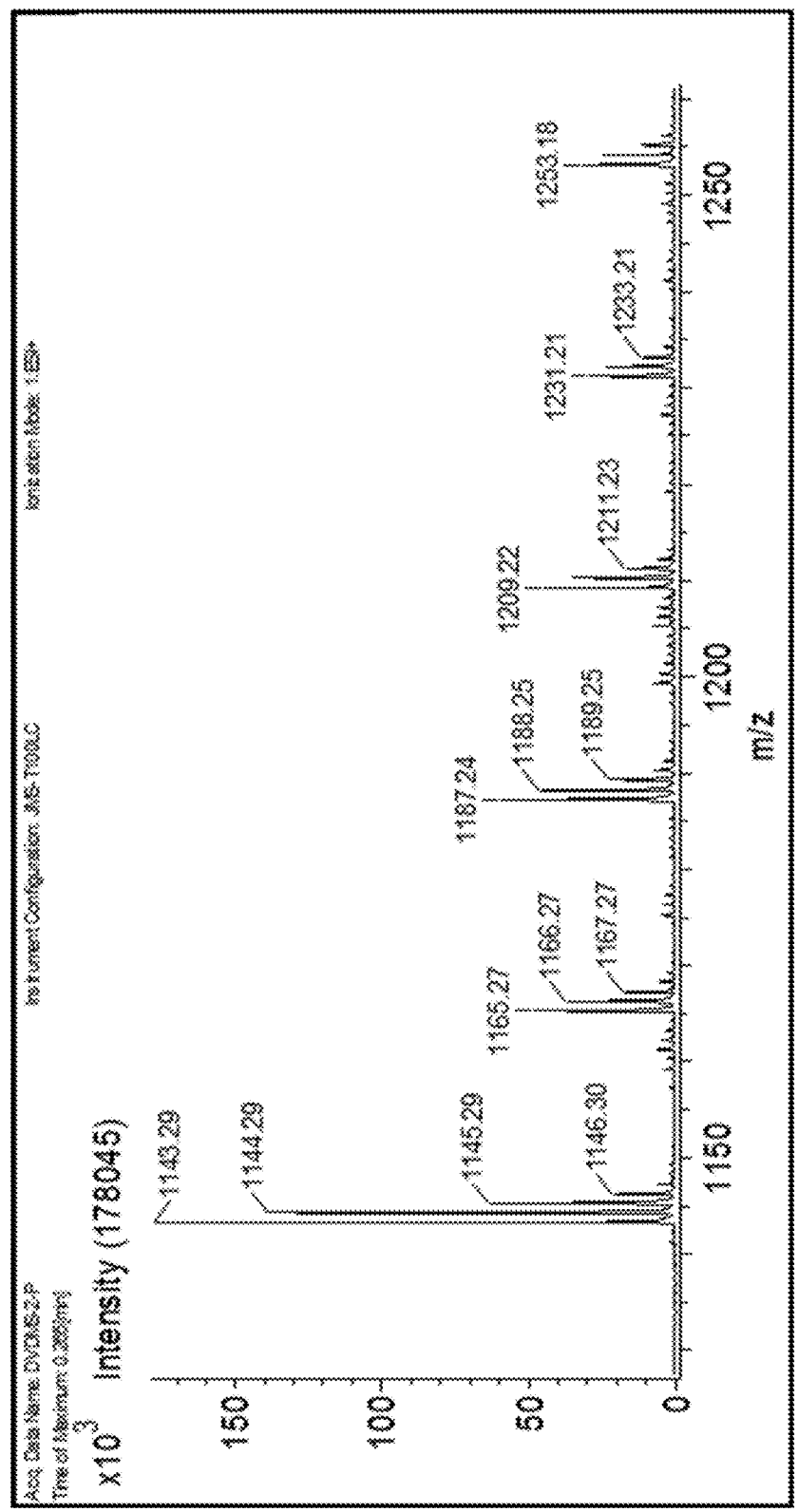
FIG. 2 shows a cold spray mass spectrum of the compound of the compound of FIG. 1.
Figure 3:
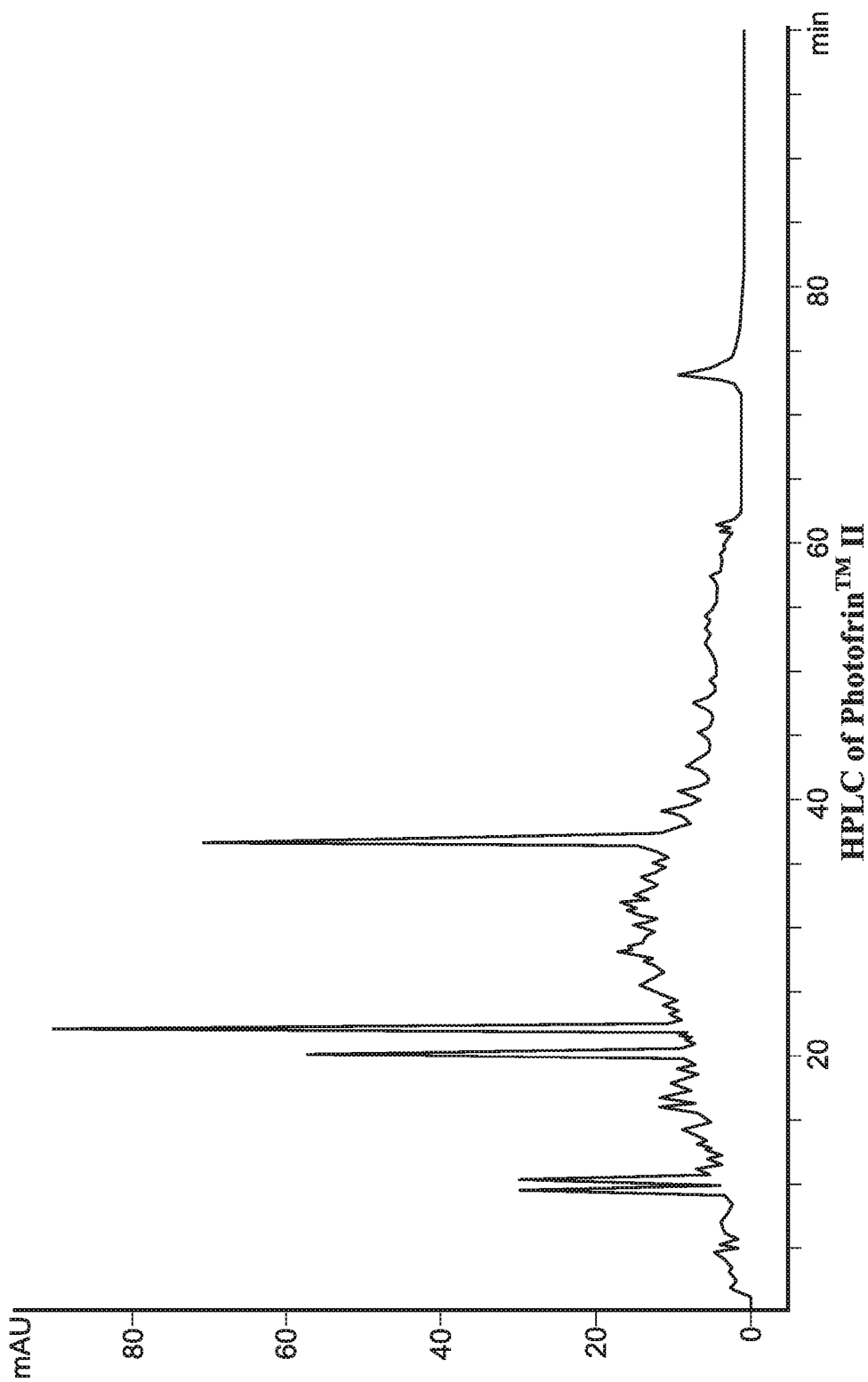
FIG. 3 show an HPLC elution for Photofrin™ II. It is clear that Photofrin™ is a mixture of many different compounds eluting at various times.

A cold mass spectrometer graph for DVDMS can be seen in FIG. 2; The graph was obtained using a CSI ion source; spray temperature is room temperature at 25° C.; desolvation temperature at 250° C.; the solvent used was methanol; and DVDMS concentration was 40 ng/μl.

Cold spray MS M/Z: 1253.18 $[M+Na]^+$, 1231.21 $[M+H]^+$, 1209.22$[M+2H-Na]^+$, 1187.24$[M+3H-2Na]^+$, 1165.27 $[M+4H-3Na]^+$, 1143.29$[M+5H-4Na]^+$.

The cold spray MS analysis demonstrates that the chemical structure of Bis [1-[6,7-bis [2-(sodiumcarbonate)ethyl] 1,3,5,8,-tetra-methyl-2-vinyl-porphin-4-yl]-ethy]ether (DVDMS) is as shown in FIG. 2.

Examples: Administration and Use

Example 2

Two kinds of leukemia cells (K562, U937) as main tumor cell models and cells (peripheral blood mononuclear cells, spleen lymphocytes) separated from healthy ICR mice as normal cell models were used. The multivolume spectrophotometer system and fluorescence spectrophotometer were used to determine the spectral characteristics of DVDMS. The uptake of DVDMS by tumor cells and normal cells was measured by flow cytometry. The MTT assay was used to examine the cytotoxicity and sonotoxicity of DVDMS. The absorption spectra showed that DVDMS had five distinct peaks at 359, 514, 548, 580, and 631 nm, respectively, and the maximum peak was at B359 nm. The fluorescence emission spectra showed that DVDMS fluorescence emission was at 642 nm. DVDMS showed an advantage of quick cellular uptake and selective accumulation in tumor cells compared with normal healthy cells. The cytotoxicity of DVDMS by the MTT method was dose dependent, and DVDMS had little cytotoxicity to normal cells. The sonotoxicity of DVDMS showed that in the presence of DVDMS, under appropriate conditions, the cell-damaging effect of ultrasound was significantly enhanced. The present study showed that the newly synthesized sensitizer, DVDMS, under appropriate experimental conditions, can act as a potential sonosensitizer for tumors in sonodynamic therapy.

Example 3

DVDMS showed higher autofluorescence intensity and singlet oxygen production efficiency compared with other photosensitizers in both cancerous and normal cells. Compared with hematoporphyrin, DVDMS-mediated SDT was more cytotoxic in ECA-109 cells. Abundant intracellular reactive oxygen species (ROS) was found in the SDT groups, and the cytotoxicity induced by SDT was effectively remitted by ROS scavengers. DVDMS located mainly to the mitochondria of ECA-109 cells, which were seriously damaged after exposure to SDT. Release of cytochrome C, an increased rate of apoptosis, and activated apoptosis protein were detected in the SDT group. In addition, relatively severe cell damage was observed on scanning electron microscopy after treatment with DVDMS and SDT. These results suggest that DVDMS can be activated by ultrasound, and that DVDMS mediates SDT-induced mitochondrial-dependent apoptosis in ECA-109 cells via production of ROS.

Example 4

The purpose of this study was to evaluate the sonodynamically induced antitumor effect of a novel sonosensitizer (DVDMS) in mice bearing sarcoma 180 solid tumors. In order to determine the optimum timing of ultrasound exposure after administration of DVDMS, a three-dimensional optical imaging system (IVIS spectrum) was used to observe the biodistribution of DVDMS in S180 tumor. The antitumor effects were estimated by the tumor inhibition ratio (volume and weight) after sonodynamic therapy. The experiments suggested that DVDMS has a preferential localization in tumors, but a low accumulation in most normal tissues. A significant synergistic effect of ultrasound combined with DVDMS was obtained when the load power indicated 4 W and DVDMS dose was above 2 mg/kg. At day 14 after DVDMS-SDT, the tumor volume inhibition ratio was 56.27%. In addition, the tumor weight inhibition ratio after the synergistic treatment was 55.37%, Which was obviously stronger than ultrasound treatment alone (23.85%) and DVDMS alone (23.15%). Moreover, no metastasis occurred to the tumors in the SDT-treated mice compared with the control group. Conclusions: DVDMS is a potential sensitizer for sonodynamic cancer therapy. The antitumor effect of ultrasound could be enhanced in the presence of DVDMS, which might be involved in a sonochemical mechanism.

Example 5

At the beginning, we have pointed out that DVDMS is an active component isolated from Photofrin™ II. So it would be very interesting to compare the in vivo anti-cancer efficacy of DVDMS-PDT with PHOTOFRIN™-PDT (PF-PDT). The results showed that DVDMS-PDT significantly prolonged the survival of the 4T1 mammary cancer-bearing mice compared to control and DVDMS-only groups (p<0.01). DVDMS-PDT was also more effective than PF-PDT at increasing the survival of tumor-bearing mice (p<0.05).

PDT with DVDMS significantly inhibited tumor growth: Tumor-bearing mice were divided into eight experimental groups to examine DVDMS-PDT phototoxicity in vivo and compare these effects with PF-PDT. Representative mice were photographed at 6, 12, or 18 days after the corresponding treatments. The group treated with 2 mg/kg DVDMS only exhibited tumor growth similar to that in the control group, indicating that tumor growth was not affected by DVDMS injection without irradiation. However, tumor size decreased in a dose-dependent manner with increasing DVDMS and light exposure. Using the same light exposure (100 J/cm$^2$), the tumor size in the 2 mg/kg DVDMS group was less than in the 10 mg/kg PF group, suggesting that DVDMS has an antitumor efficiency superior to PF.

The tumor volume and tumor weight results were evaluated for each group.

Nineteen days after treatment, the tumor volume and tumor weight of 4T1 tumors were significantly lower in the DVDMS plus light exposure groups than in the control or DVDMS alone groups. As predicted, these effects exhibited a DVDMS-concentration and light-dose dependence. Using the same light exposure dose, PDT with 2 mg/kg DVDMS had a greater effect than PDT with PF at 10 mg/kg. On the 17th day, the tumor volume inhibition ratios in the (1) 2 mg/kg DVDMS alone, (2) mg/kg DVDMS+50 J/cm$^2$, (3) 1 mg/kg DVDMS+50 J/cm$^2$, (4) 2 mg/kg DVDMS+50 J/cm$^2$, (5) 2 mg/kg DVDMS+100 J/cm$^2$, (6) 2 mg/kg DVDMS+150 J/cm$^2$ and (7) 10 mg/kg PF+100 J/cm$^2$ groups as compared with the control were 7.42%, 18.61%, 38.51%, 59.23%, 66.97%, 78.12%, 38.76%, respectively. On the 19th day, the tumors were photographed and the average tumor weight in each group was calculated. The results showed that the trend of tumor weight inhibition was consistent with tumor volume inhibition.

The treatment of brain stem tumors has long represented a troublesome area in the medical world. Since the brain stem is situated in a central region of the brain, there are many important neural clusters as well as many axons connecting important parts of the brain, and is consequently an area critical for human survival. Tumors that arise here, however small, often induce severe clinical symptoms, with high rates of both mortality and disability. To date, neurosurgeons have been wholly unable to treat brain stem tumors, being only to palliative care. However, the advent of sonodynamic therapy (SDT) promises to completely change this situation. In extensive testing of SDT treatment for brain stem tumors, tumors have showed a marked stop growth, and in many cases, one to two months after treatment, tumors shrink and patients show significant improvement both in clinical symptoms and in overall condition. Better yet, SDT is also extremely safe for a non-invasive treatment procedure, with a highly discriminate ability to eliminate cancer cells without impacting healthy tissue. With prompt treatment, SDT can, with high probability, induce full remission while simultaneously preserving a high quality of life. Moreover, SDT has a pronounced effect in the treatment of pituitary gland tumors and optical nerve glioma, making possible treatment for the first time of many brain tumors without invasive surgery.

Multiple treatments may be used without significant side effects. e.g. any number from one to eight treatments may be used.

Dosage is by body weight and may be e.g. from 0.1 to 0.5 mg/kg, preferably from 0.15 to 0.35 mg/kg and most preferably from 0.15 to 0.25 mg/kg.

Administration is by IV injection. The DVDMS may be suspended or dissolved in a biocompatible liquid, e.g. an isotonic fluid or plasma or plasma substitute or used directly as a powder.

The ultrasound frequency may be from 0.25 to 1.25 MHz and preferably from 0.5 to 1 MHz and the ultrasound power may be from 0.1 W/cm$^2$ to 1.5 W/cm$^2$.

Below are two typical clinical cases where SDT was selected for treatment of tumors of the brain stem.

For Photofrin™ the dosage was 2 mg/kg of body weight. For DVDMS, the dosage was 0.2 mg/kg of body weight, a factor of ten less than Photofrin™.

The ultrasound frequency was 0.5 to 1 MHz and the ultrasound power was 0.1 W/cm$^2$ to 1.5 W/cm$^2$.

Ultrasound treatment is delayed after injection to permit absorbance of the sonodynamic compound into the tumor or other hyperproliferative tissue. In the case of Photofrin™ the delay is extensive, e.g. 20 to 30 hours. In the case of DVDMS, absorbance is much quicker allowing ultrasound treatment in e.g. from 1.5 to 2.5 hours.

Multiple treatments may be used without significant side effects, e.g. any number from one to eight treatments may be used.

Due to differential absorption times into tumor, patient was intravenously injected with Photofrin™ 24 hours before ultrasound treatment and DVDMS was intravenously injected two hours prior to ultrasound treatment.

Treatment occurred each time for 20-30 minutes and total time to treat three times was 72 hours.

Example 6

Case one: Photofrin™-SDT

Figure 8A:
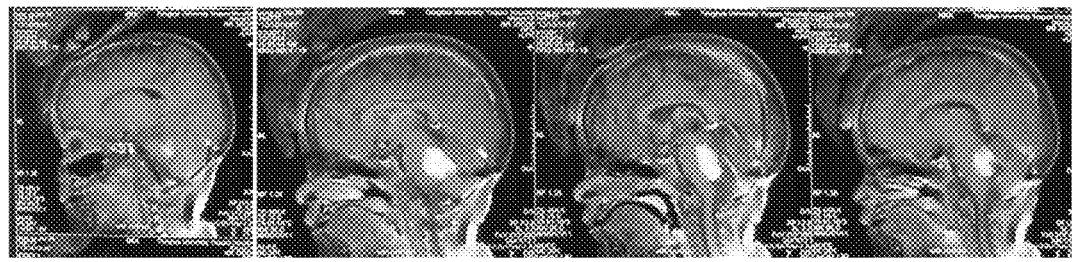
FIG. 8A is an MRI showing size of tumor in a 6 year old female patient before SDT treatment with Photofrin™ II.

Patient 6 years old, female, cerebellar vermis astrocytoma (III stage) having invaded the dorsal brainstem. Surgical resection was successful only against the vermis tumors, with the brain stem tumor left intact. Size of remaining tumor indicated by MRI before SDT treatment: 3×2×3 cm. See FIG. 8A.

Figure 4:
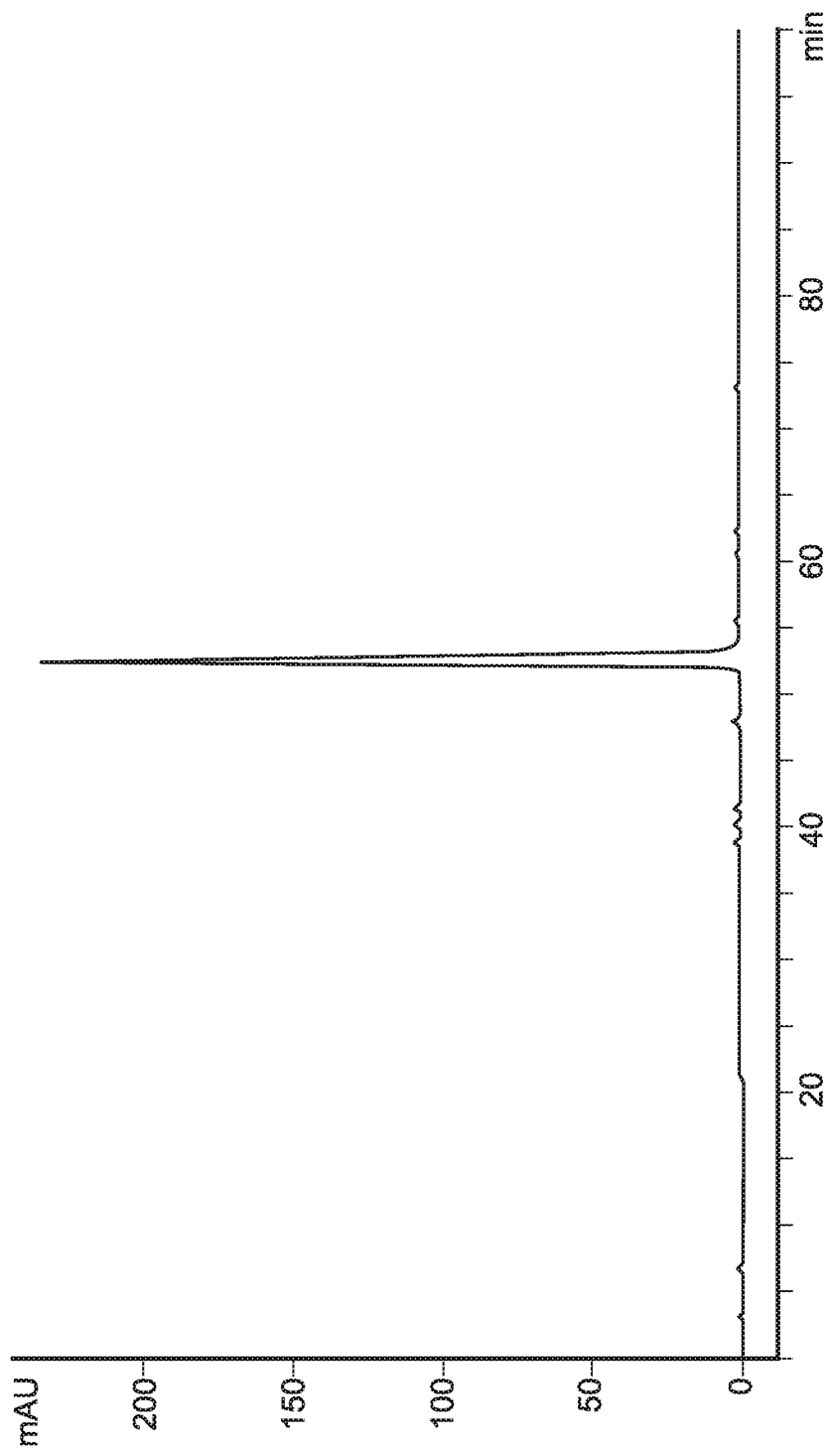
FIG. 4 shows an HPLC elution of protoporphyrin dimethyl ester. (DVDMS).
Figure 5:
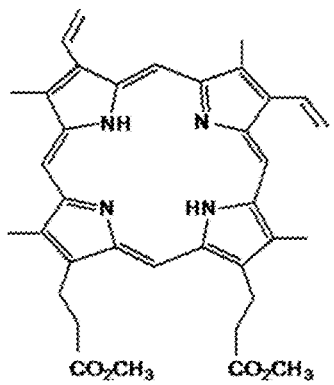
FIG. 5 shows a reaction scheme for preparation of DVDMS from protoporphyrin dimethyl ester.
Figure 5:
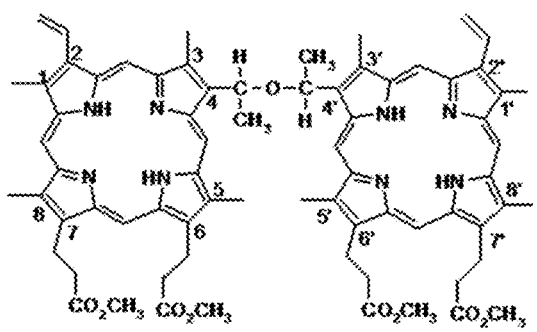
Figure 5:
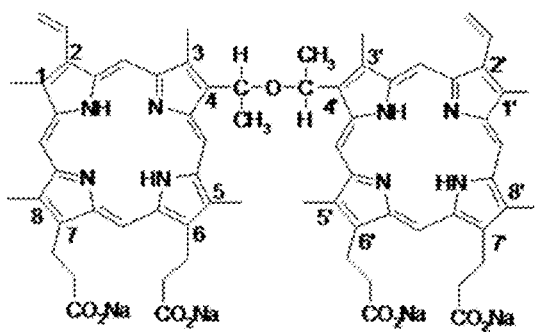
Figure 8B:
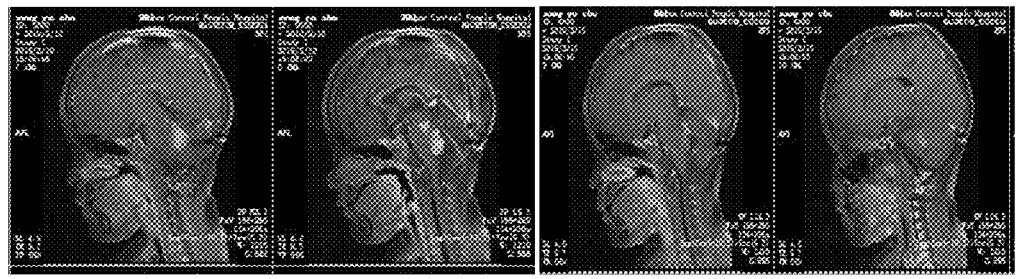
FIG. 8B is an MRI showing tumor size 60 days after SDT treatment with Photofrin™ II.
Figure 8C:
FIG. 8C is an MRI showing tumor size 4 months after SDT treatment with Photofrin™ II.

60 days after Photoftin-SDT treatment resulted in marked reduction in tumor size and blood vessels associated with the tumor shrank by 70%. See FIG. 8B 4 months after SDT treatment, almost complete elimination of tumor blood vessels and absorption of tumor occurred. See FIG. 8C.

Example 7

Case 2: Sinoporphyrin Sodium-SDT (DVDMS)

Figure 9A:
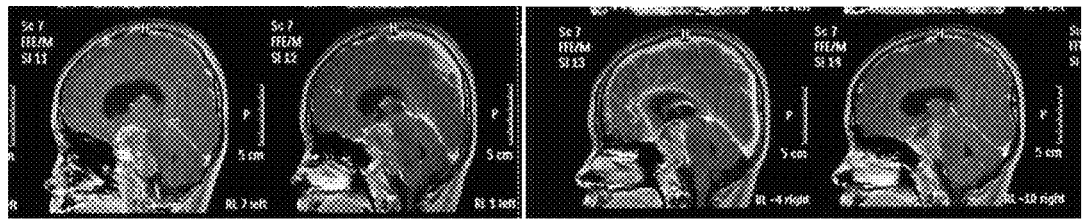
FIG. 9A is an MRI showing brain stem tumor lesions in an 11 year old female patient.

Female patient, aged 11. Symptoms included a severe headache with no known cause, vomiting, and bilateral weakness of lower extremities. The ventral brain stem was examined and brain MRI lesions' grew into a rich blood supply the brain stem, with significant brain stem edema and hydrocephalus. A right ventricle peritoneal shunt (Shunt) was used to treat headache symptoms, but hydrocephalus remained evident. See FIG. 9A.

Figure 9B:
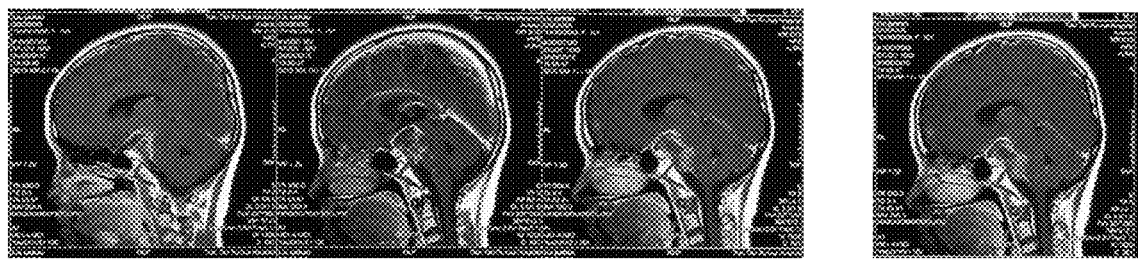
FIG. 9B is an MRI showing the brain stem after treatment with DVDMS.

On review after the Sinoporphyrin sodium-SDT treatment, the cranial MRI indicated that the tumor was absorbed, brain stem edema was significantly reduced, with the ventricular morphology restored to near normal. Neurological examination was normal. See FIG. 9B.

Figure 9C:
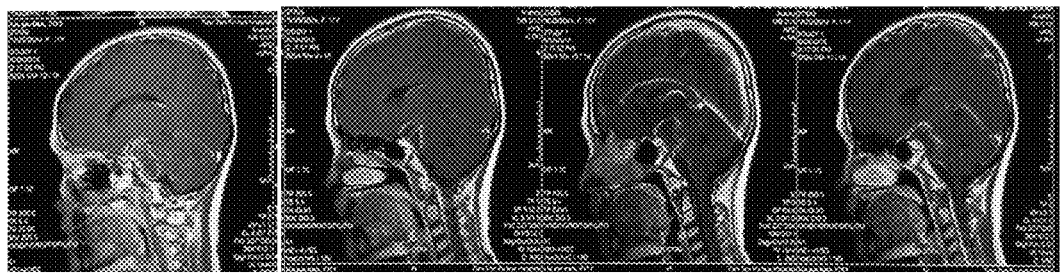
FIG. 9C is an MRI showing the brain stem 30 days after treatment with DVDMS. The MRI shows that the ventral brain stem tumor has disappeared, that the tumor blood vessels have disappeared, that the brain stem edema has disappeared, that hydrocephalus has disappeared and that cerebral aqueduct oppression has lifted.

Sound power for 30 days after the review of the head MRI examination revealed: the ventral brain stem tumor disappeared. Brain stem implant disappearance of tumor blood vessels, brain stem edema disappeared, hydrocephalus disappearance of the cerebral aqueduct oppression lifted. The patients was able to return to school and the activities of normal life. See FIG. 9C.

It should be noted that treatment with DVDMS accomplished what appears to be complete remission within only 30 days but the use of Photofrin™ required 4 months for almost complete remission.

Sinoporphyrin sodium (DVDMS) is a single-compound substance, with purity over 98%, a therapeutic dosage at 0.2 mg/kg of body weight, and high quality control. Photofrin, in comparison, is a mixture of more than 20 porphyrin derivatives, whose therapeutic dosage at 2 mg/kg of body weight is 10 times that of Sinoporphyrin Sodium.

Also Photofrin's components last in the skin for more than 4 weeks, inducing side effects of dermatological phototoxicity, potentially resulting in rashes, blisters, hyperpigmentation, and in severe cases inducing skin ulceration and results in the patient, after administration of the treatment, requiring 4-6 weeks avoidance of direct sunlight, eye examinations, as well as dental work requiring dental lamps, but compare with Photofrin, Sinoporphyrin Sodium (DVDMS) has both high efficacy and low toxicity, lacking dermatological phototoxicity.

The results mentioned above show that DVDMS is not only one of the active components of Photofrin™ II for PDT but unexpectedly is also an efficient sonosensitizer for SDT. That means DVDMS is a doubly promising activation agent that can be used for activated cancer therapy.

What is claimed is:

1. A method for treatment of hyperproliferative tissue in vivo by i.v. injection of purified bis [1-[6,7-bis [2-(sodium carbonate ethyl]-1,3,5,8-tetramethyl-2-vinyl-porphin-4-yl] ethyl] ether (DVDMS) in a biocompatible liquid at 0.1 to 0.5 mg of DVDMS per kg of body weight and subsequently exposing the hyperproliferative tissue to an ultrasound frequency of 0.25 to 1.25 MHz at a power 0.0.1 to 1.5 W/cm$^2$ to obtain what appears by MiII to be complete remission.

2. The method of claim 1 wherein the purity of DVDMS is at least 95%.

3. The method of claim 2 wherein the injection is by IV at a dosage of from 0.15 to 0.25 mg/kg and the hyperproliferative tissue is tumor tissue.

4. The method of claim 3 wherein the sonic frequency is from 0.5 to 1 MHz and the ultrasound power is from 0.1 W/cm$^2$ to 1.5 W/cm$^2$.

5. The method of claim 4 where the time of treatment is 20 to 30 minutes 1.5 to 2.5 hours post injection.

6. Purified bis [1-[6,7-bis [2-(sodium carbonate ethyl]-1,3,5,8, tetramethyl-2-vinyl-porphin-4-yl] ethyl] ether (DVDMS) for use in sonodynamic therapy where the purity is at least 98%.

7. The method of claim 3 wherein the tumor tissue is brain stem tumor tissue.

8. The method of claim 1 where the dosage is 0.15 to 0.25 mg/kg.

9. The method of claim 7 where the time of treatment is 20 to 30 minutes 1.5 to 2.5 hours post injection.

* * * * *